United States Patent
Greenberg et al.

(10) Patent No.: US 11,369,994 B2
(45) Date of Patent: Jun. 28, 2022

(54) MEMS-SWITCHED ULTRASONIC TRANSDUCER ARRAY WITH IMPROVED RELIABILITY

(71) Applicants: Adi Greenberg, Haifa (IL); Yoav Levy, Hinanit (IL)

(72) Inventors: Adi Greenberg, Haifa (IL); Yoav Levy, Hinanit (IL)

(73) Assignee: Insightec, Ltd., Tirat Carmel (IL)

( * ) Notice: Subject to any disclaimer, the term of this patent is extended or adjusted under 35 U.S.C. 154(b) by 898 days.

(21) Appl. No.: 16/153,024

(22) Filed: Oct. 5, 2018

(65) Prior Publication Data

US 2020/0108412 A1   Apr. 9, 2020

(51) Int. Cl.
*B06B 1/06* (2006.01)
*A61N 7/00* (2006.01)
*B06B 1/02* (2006.01)
*H01L 41/187* (2006.01)

(52) U.S. Cl.
CPC ............ *B06B 1/0622* (2013.01); *A61N 7/00* (2013.01); *B06B 1/0215* (2013.01); *B06B 2201/76* (2013.01); *H01L 41/1876* (2013.01)

(58) Field of Classification Search
CPC .. B06B 1/0622; B06B 1/0215; H01L 41/1876
See application file for complete search history.

(56) References Cited

U.S. PATENT DOCUMENTS

| | | | |
|---|---|---|---|
| 2005/0017599 A1* | 1/2005 | Puskas | B06B 1/0618 310/317 |
| 2006/0058672 A1* | 3/2006 | Klepper | G01S 15/8915 600/447 |
| 2016/0100822 A1* | 4/2016 | Kim | G01S 7/52046 600/472 |
| 2016/0157818 A1* | 6/2016 | Cho | A61B 8/4444 600/443 |

OTHER PUBLICATIONS

Liu Yuhao et al.: "RF MEMS switch for Reconfigurable RF-Front End with Improved Hot-Switching Capabilities", 2018 IEEE International Symposium On Antennas and Propagation & USNC/URSI National Radio Science Meeting, IEEE, Jul. 8, 2018 (Jul. 8, 2018), pp. 1237-1238.
International Search Report and the Written Opinion for International Application No. PCT/IB2019/000978 dated Jan. 27, 2020, 13 pages.
Insightec, Ltd., International Preliminary Report on Patentability, PCTIB2019/000978, dated Mar. 23, 2021, 10 pgs.

* cited by examiner

*Primary Examiner* — Bryan P Gordon
(74) *Attorney, Agent, or Firm* — Morgan, Lewis & Bockius, LLP

(57) ABSTRACT

Various approaches for improving reliability in an ultrasound system having transducer elements, phase transmission lines, and a switch matrix having beamforming switches for connecting the phase transmission lines to the transducer elements involve operating the beamforming switches to avoid "hot" switching as the activation pattern of the transducers changes.

24 Claims, 8 Drawing Sheets

MEMS-SWITCHED ULTRASONIC TRANSDUCER ARRAY WITH IMPROVED RELIABILITY

FIELD OF THE INVENTION

The field of the invention relates generally to ultrasound systems and, more particularly, to systems and methods involving phased arrays of ultrasound transducers implementing switches manufactured using microelectromechanical systems (MEMS) technology.

BACKGROUND

Focused ultrasound (i.e., acoustic waves having a frequency greater than about 20 kHz) can be used to image or therapeutically treat a patient's internal body tissues. For example, ultrasound waves may be used in applications involving ablation of tumors, thereby eliminating the need for invasive surgery; targeted drug delivery; control of the blood-brain barrier; lysing of clots; and other surgical procedures. During treatment, a piezoceramic transducer is either placed inside of the patient's body or, more generally, externally to the patient but in close proximity to the tissue to be ablated (i.e., the target). The transducer converts an electronic drive signal into mechanical vibrations, resulting in the emission of acoustic waves. The transducer may be geometrically shaped and positioned along with other such transducers so that the ultrasound energy they emit collectively forms a focused beam at a "focal zone" corresponding to (or within) the target tissue region. Alternatively or additionally, a single transducer may be formed of a plurality of individually driven transducer elements whose phases can each be controlled independently. Such a "phased-array" transducer facilitates steering the focal zone to different locations by adjusting the relative phases among the transducers. As used herein, the term "element" means either an individual transducer in an array or an independently drivable portion of a single transducer.

By way of illustration, FIG. 1 is a simplified schematic representation of an exemplary focused ultrasound system 100 used to generate and deliver a focused acoustic energy beam to a targeted region 102. The system 100 includes a phased array 104 having a large number of transducer elements 106, a beamformer 108 driving the elements 106 in the phased array 104, a controller 110 in communication with the beamformer 108, and supporting circuitry (e.g., a frequency generator)112. In some embodiments, the system further includes an imager 114, such as a magnetic resonance imaging (MRI) device, a computer tomography (CT) device, a positron emission tomography (PET) device, a single-photon emission computed tomography (SPECT) device, or an ultrasonography device, for determining anatomical characteristics and/or monitoring treatment effects of the target region 102 where ultrasound will be focused.

The array 104 may have a curved (e.g., spherical or parabolic) shape, but may include one or more planar or otherwise shaped sections. Its dimensions may vary, depending on the application, between millimeters and tens of centimeters. The transducer elements of the array 104 may be piezoelectric ceramic elements (indicated as PZT in the figure), and may be mounted in silicone rubber or any other material suitable for damping the mechanical coupling between the elements. Piezo-composite materials, or generally any materials capable of converting electrical energy to acoustic energy, may also be used.

The transducer array 104 is coupled to the beamformer 108, which drives the individual transducer elements 106 so that they collectively produce a focused ultrasonic beam or field at the targeted region 102. For n transducer elements, the beamformer 108 may contain n driver circuits, each including a drive signal having a relative amplitude and phase driving one of the transducer elements in the transducer array 104. The beamformer 108 receives a radio frequency (RF) input signal, typically in the range from 0.1 MHz to 10 MHz, from the supporting circuitry (e.g., a frequency generator) 112. In some embodiments, the frequency generator 112 is integrated with the beamformer 108. The radio frequency generator 112 and the beamformer 108 are configured to drive the individual transducer elements 106 of the transducer array 104 at the same frequency, but at different phases and/or different amplitudes.

The amplification or attenuation factors $\alpha_1$-$\alpha_n$ and the phase shifts $\varphi_1$-$\varphi_n$ imposed by the beamformer 108 serve to transmit and focus ultrasonic energy on a selected anatomical region (e.g., the target region 102). The amplification factors and phase shifts are computed using the controller 110, which may provide the computational functions through software, hardware, firmware, hardwiring, or any combination thereof. For example, the controller 110 may utilize a general-purpose or special-purpose digital data processor programmed with software in a conventional manner, and without undue experimentation, in order to determine the phase shifts and amplification factors necessary to obtain a desired focus or any other desired spatial field patterns.

Thus, the controller 110 determines which transducer elements are active at any time, and the phase and amplitude of the signal applied to them. This necessitates a switch matrix 116 capable of quickly and reliably energizing and de-energizing selected transducer elements 106 by coupling them to corresponding drive circuits 120 or grounding them. The switches must be capable of tolerating the high signal amplitudes (e.g., 80V in the setup of FIG. 1) at which the drive circuits 120 operate, remain immune to system noise, and operate with sufficient reliability to ensure patient safety. Traditional switching solutions for such applications include solid state complementary metal-oxide-semiconductor (CMOS) switches and electromechanical relays. But standard silicon-based CMOS switches suffer from significant parasitic capacitance and resistance. Relays, on the other hand, have limited actuation lifetimes, a limited number of channels, and large package sizes. Switches based on microelectromechanical systems (MEMS) technology, although known for decades, have only recently become available as commercial devices offering high performance. MEMS switches offer very small form factors and minuscule actuation movements that can tolerate very large numbers of on-off cycles.

In particular, MEMS switches typically utilize an electrostatically actuated, micromachined cantilever beam switching element, which operates, in effect, as a micrometer-scale mechanical relay with metal-to-metal contacts actuated via electrostatics. The terminals of a MEMS switch can be thought of as a source, gate, and drain. When a DC voltage is applied to the gate, an electrostatic pull-down force is generated on the switch beam. When the gate voltage ramps to a high enough value, it creates enough attraction force to overcome the resistive spring force of the switch beam, and the beam starts to move down until the contact touches the drain, turning the switch on. When the gate voltage is removed, the electrostatic attraction force disappears, and the switch beam acts as a spring with sufficient restoring force to open the connection between the source and the drain, thereby turning the switch off.

When deployed in large numbers in a system such as that described above, with the reliability requirements of a medical device, switch matrices composed of MEMS switches can exhibit certain limitations. For example, when the ultrasound parameters (e.g., phase shifts) are adjusted in conventional systems, generally, the transducer elements 106 are simply disconnected from the ultrasound control circuitry via opening corresponding beamforming switches in the switch matrix 116. When disconnected, a voltage may be present on the switches from various sources, such as RF signals, reflections, and/or thermal or mechanical stress; this may result in a "hot" switch that can undergo premature failure. In general, MEMS switches are sensitive to the switching voltage present on the switch contacts during actuation. For example, when the switching voltage is below 1V, the lifetime of the MEMS switch may surpass 1 billion cycles, whereas if the switching voltage is raised to 10V, the switch lifetime may drop below 100 million cycles. Therefore, it is desirable to minimize the switching voltage in MEMS switches. Accordingly, there is a need for an approach that minimizes the switching voltage in MEMS switches during actuation without compromising reliability or switching speed.

SUMMARY

The present invention provides systems and methods for operating an ultrasound system in a manner that limits the switching voltages of the beamforming switches in the switch matrix. As used herein, changing the states of the beamforming switches may include, for example, coupling various phase transmission lines to an electrical ground or to the same or different transducer elements for generating one or more foci at one or more desired target locations with a target focal profile (e.g., a target focal intensity, focal shape, focal size, and/or focal location). This approach, sometimes referred to as "cold switching," enhances the lifetimes of the beamforming switches (in particular MEMS switches), thereby advantageously improving the reliability and durability of the ultrasound system.

It is found that switch life may be extended not only by minimizing the absolute voltage level on a particular switch, but also by minimizing the voltage difference between multiple switches connected to the same transducer element. That is, a voltage difference among switches connected in parallel can be harmful even at low overall voltages.

As explained above, the ultrasound transducer elements are driven at phases computed to produce a focus at a desired location. In typical systems, rather than generate a separate signal with the correct phase for each transducer, a time-varying (e.g., sinusoidal) driver signal produced by a signal generator is fed through a series of phase transmission lines to produce a set of basis signals having different phase offsets. These phase transmission lines are selectively coupled to the transducer elements so as to drive the transducer elements at the desired phases, thereby generating a focus at the desired location (e.g., the target region). To accomplish this, each transducer element is served by a dedicated set of beamforming switches equal in number to the number of basis signals. (Consequently, the number of switches in the switch matrix is the number of basis signals multiplied by the number of transducer elements.) As a result, all the transducer elements are connected to sets of beamforming switches in parallel; for each transducer element, only one of the beamforming switch is activated (or closed) in each set. The closed beamforming switches connect the transducer elements to the proper basis signals so that the outputs of all transducer elements will achieve the desired focus. In accordance with embodiments of the invention, precautions are taken with respect to the switches within each set. For example, when it is time to change the connection pattern of switches to transducer elements in order to change the ultrasound focus, the voltage produced by the signal generator may first be reduced (not necessarily to zero). If the currently closed beamforming switches are opened at this time, a voltage may be present on the switches, thereby causing damage thereto. In addition, for each transducer element, the voltage difference between the currently closed switch that is to be later opened and the currently open switch that is to be later closed may be harmful. Hence, in various embodiments, the voltage across the beamforming switches may be reduced by, for example, sequentially closing the beamforming switches that are to be later closed (in accordance with a new switch pattern) on an element-by-element basis before the currently closed switches that are to be later opened change state. In this way, grounding or other voltage-reduction measures will have a uniform effect, so that all beamforming switches associated with an individual transducer element will be at substantially the same voltage (even if this voltage is not zero volts) before the currently closed switches are opened. Because the procedure is sequential, some of the beamforming switches will experience greater cumulative voltages over time than others if the procedure is repeated identically each time. Thus, discharge strategies may be adopted to ensure that, on average, the switches are exposed to similar voltage burdens.

Additionally or alternatively, the output of the different phase transmission lines may be progressively coupled, one to the next, so that the voltage between switches will not be affected by phase differences. This sequential coupling may take place at the phase generator or by differential switches; each differential switch may be associated with a phase transmission line and may couple the phase transmission line to ground, a common voltage, or another transmission line. Accordingly, the voltage difference between the coupled transmission lines (and thereby the beamforming switches associated therewith) can be eliminated (or at least reduced). In some embodiments, sequential coupling of the phase transmission lines may occur prior to closing the beamforming switches that are to be later closed in accordance with a new switch pattern. Certain differential switches may be designated as sacrificial, and the strategy is reversed to concentrate the voltage burden on the sacrificial switches, which are conveniently replaced together.

In one implementation, in the first stage when the output voltage of the signal generator is reduced, the ultrasound system may remain in its current state (e.g., delivering the current pattern of sonications) for a duration (e.g., 1 microsecond-1 millisecond) until a substantial portion (e.g., 90%, 80% or 70%) of the reflection energy has dissipated. In one embodiment, the reflection energy is determined to be substantially dissipated when the measured voltage is closer to zero than, for example, ±0.5V. Subsequently, the beamforming switches that are to be closed in accordance with the new switch pattern may be closed. Additionally or alternatively, the phase transmission lines may be sequentially coupled one to another using, for example, differential switches. As used herein, differential switches refer to switches that ground or couple the phase transmission lines to one another so as to substantially equalize the voltages on the coupled transmission lines. The differential switches may be MEMS switches or CMOS switches. Only after the voltage in all currently activated beamforming switches is closer to zero than, for example, ±0.5V (or less) or the beamforming switches can be assumed to have settled is the switch pattern changed so that different basis signals are now connected to the transducer elements to produce a focus at a new location. The ultrasound system is then ready to transmit energy to the new focus in accordance with the treatment procedure.

Accordingly, in one aspect, the invention pertains to a method of improving reliability in an ultrasound system that includes (i) multiple transducer elements, (ii) a phase generator connected to multiple phase transmission lines, and (iii) a switch matrix including multiple beamforming switches for switchably connecting various ones of the phase transmission lines to the transducer elements; each of the transducer elements is associated with a set of beamforming switches each connected to a different phase transmission line, and some of the beamforming switches are open and some of the beamforming switches are closed in accordance with an initial switch activation pattern. In various embodiments, the method includes (a) reducing the differential voltage between the phases at the phase generator; (b) reducing the differential voltage between the phases at near the beamforming switches; and (c) following steps (a) and (b), altering the initial switch activation pattern. In one implementation, the differential voltage in step (a) is reduced below the first predetermined threshold corresponding to a voltage closer to zero than ±0.5V. In addition, the differential voltage in step (b) may be reduced below the second predetermined threshold corresponding to a voltage closer to zero than ±0.5V.

In some embodiments, the method further includes a step of pausing after performing steps (a) and (b) and before performing step (c). The pausing step may have a duration determined by an environmental condition (e.g., an ambient RF level or reflection from the transducer elements) and/or a sonication parameter (e.g., an amplitude of a pulse transmitted from one of the transducer elements). As used herein, the term "ambient RF level" means RF signals detectable by an RF detection device situated in proximity to the ultrasound transducer. Additionally, the method may include the step of monitoring a voltage on a closed switch; the environmental condition is a magnitude of the monitored voltage. Additionally or alternatively, the method may further include a step of pausing after performing step (a) and before performing step (b).

In various embodiments, step (b) is performed by progressively connecting the phase transmission lines together using multiple differential switches, each differential switch being associated with one or more phase transmission lines. In addition, one or more beamforming switches and/or one or more differential switches may be an MEMS switch. Alternatively, one or more beamforming switches and/or one or more differential switches may be a CMOS switch. In one embodiment, the differential switches and/or the beamforming switches in each set are sequentially activated in a predetermined order. The predetermined order may be based on a previous switching order. For example, the predetermined order is determined by a number of previous times each of the differential switches was the first differential switch coupling the associated phase transmission line to another phase transmission line when changing the initial switch activation pattern to a new switch activation pattern. Additionally or alternatively, the predetermined order may be determined by a number of previous times each of the beamforming switches was the first beamforming switch that was activated when changing the initial switch activation pattern to a new switch activation pattern. In one implementation, the predetermined order is based on a number of previous times each of the differential switches in each switch set being a sacrificial switch.

In some embodiments, in a set of the beamforming switches in which the first beamforming switch is closed and the second beamforming switch is open, step (c) includes closing the second beamforming switch and, thereafter, opening the first switch. In addition, in a set of the beamforming switches in which the first group of beamforming switches is closed and the second group of beamforming switches is open, step (c) may include closing the second group of beamforming switches and, thereafter, opening the first group of beamforming switches; the beamforming switches in the second group are sequentially closed in a predetermined order. Again, the predetermined order may be based on a previous switching order. For example, the predetermined order may be determined by a number of previous times each of the beamforming switches in the second group was first to be closed. Additionally or alternatively, the predetermined order may be based on the geometry of the transducer elements (e.g., relative locations of the transducer elements within the transducer array).

In another aspect, the invention relates to an ultrasound system including an ultrasound transducer having multiple transducer elements collectively operable as a phased array; a phase generator; multiple phase transmission lines connected to the phase generator, each of the phase transmission lines having a predetermined phase shift; a matrix of beamforming switches for selectably coupling various ones of the phase transmission lines to the transducer elements, each of the transducer elements being associated with a set of beamforming switches each connected to a different phase transmission line; and a controller. In various embodiments, the controller is configured to (a) reduce an average voltage level of the phase generator below the first predetermined threshold; (b) for each set of beamforming switches, reduce a maximum voltage difference among the beamforming switches below a second predetermined threshold; and (c) detect when the voltage level is below the first predetermined threshold and the voltage difference is below the second predetermined threshold and thereupon alter an activation pattern of open and closed ones of the switches.

As used herein, the term "substantially" means ±10%, and in some embodiments, ±5%. Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. Furthermore, the particular features, structures, routines, steps, or characteristics may be combined in any suitable manner in one or more examples of the technology. The headings provided herein are for convenience only and are not intended to limit or interpret the scope or meaning of the claimed technology.

BRIEF DESCRIPTION OF THE DRAWINGS

In the drawings, like reference characters generally refer to the same parts throughout the different views. Also, the drawings are not necessarily to scale, with an emphasis instead generally being placed upon illustrating the principles of the invention. In the following description, various embodiments of the present invention are described with reference to the following drawings, in which.

DETAILED DESCRIPTION

Phased-array ultrasound transducers in accordance with various embodiments of the present invention typically include a large number (e.g., hundreds and up to thousands) of individual transducer elements whose linear dimensions in general are no greater than the wavelength of the acoustic waves generated during operation. Using small transducer elements results in increased steerability of the acoustic beam in three-dimensions—i.e., steering of both the depth of focus and the lateral focus position—over a large volume. For example, with transducer element dimensions of no more than half a wavelength, the steering angle (i.e., the maximum angle with respect to the normal of the transducer surface that can be achieved) in each direction is $\pm\pi/2$, which facilitates operation over a complete hemisphere. In certain embodiments, the transducer elements are of uniform size and shape and are evenly arranged (e.g., in a tiled fashion) so as to form an isotropic array. In other embodiments, the transducer elements are of various sizes and/or shapes and may be arranged in any suitable manner, depending on the clinical application and/or the shape and location of the patient's body to which the transducer elements are proximately placed.

Figure 1:
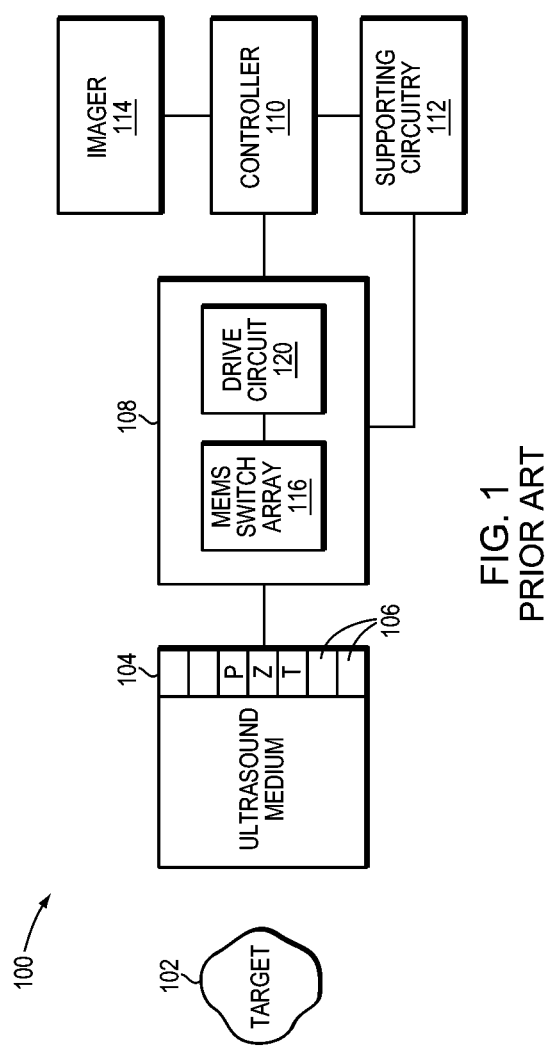
FIG. 1 illustrates a focused ultrasound system described in the prior art.
Figure 2A:
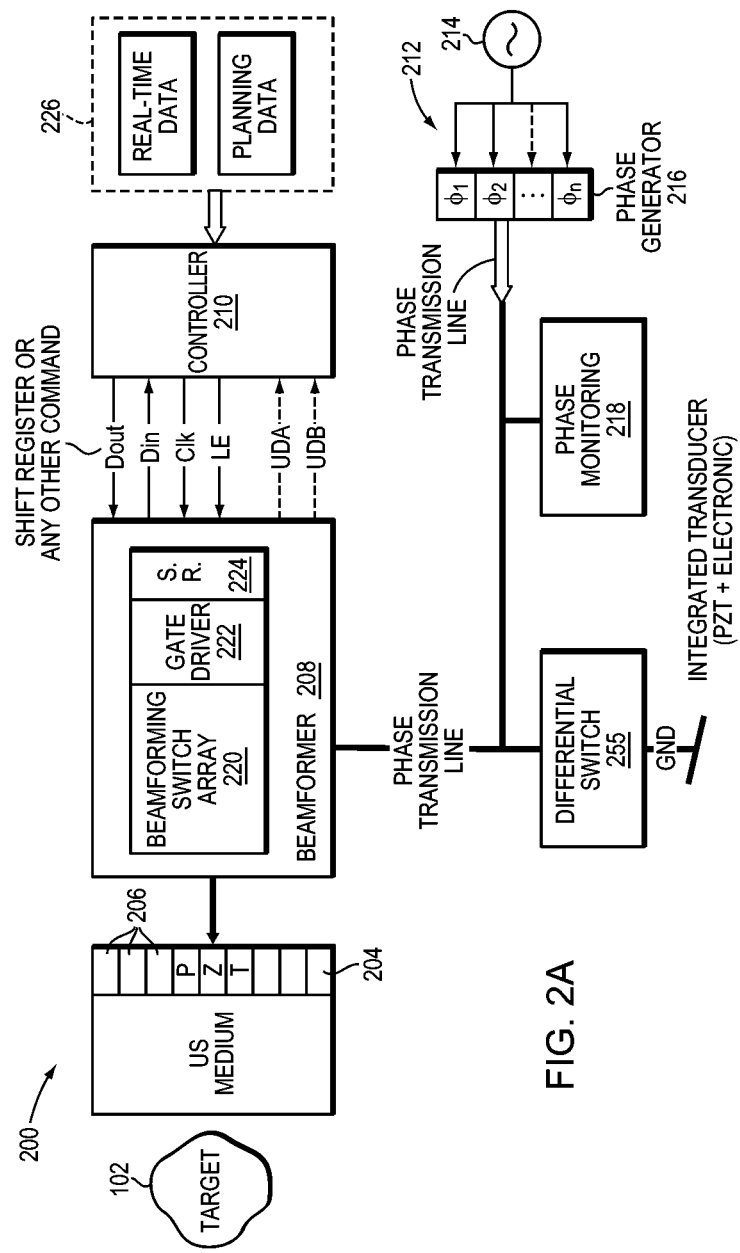
FIGS. 2A and 2B schematically depict exemplary focused ultrasound systems in accordance with various embodiments.

FIG. 2A schematically depicts an exemplary focused ultrasound system 200 in accordance with various embodiments of the present invention. Similar to conventional systems, the system 200 includes a phased array 204 of multiple transducer elements 206, a beamformer 208 driving the phased array 204, a controller 210 in communication with the beamformer 208, and supporting circuitry (e.g., a frequency generator, a phase generator, and/or any other suitable components) 212. In one embodiment, a phase generator 212 includes an AC signal source 214 and a bank of phase transmission lines 216. The phase transmission lines receive the AC signal and output the signal at a different relative phase (or a "basis" signal); these are provided to the beamformer 208. In addition, a phase monitoring circuit 218 may be implemented to monitor the phase value in each transmission line 216 coupled to one transducer element 206. In a typical deployment, the beamformer 208 includes a switching matrix 220 having multiple beamforming switches for selectively coupling and decoupling any of the phase transmission lines 216 from each one of the transducer elements 206 based on signals transmitted from gate drivers 222. The beamforming switches may be, for example, electrical switches (e.g., transistors) and/or mechanical switches. In one implementation, the beamforming switches are manufactured using microelectromechanical systems (MEMS) technology (and therefore referred to as MEMS switches herein). Alternatively, the beamforming switches may be CMOS switches.

In order to determine the pattern of switches that should be active for each transducer element 206 at any moment during treatment, the controller 210 may receive data from an application 226 running on the controller 210 itself or on a separate computer. The application 226 may provide real-time data and planning data. For example, the planning data may specify a trajectory of the focus including a desired focus path and its residence time at each target location, enabling the controller 210 to compute the phases to be applied to individual transducer elements in order to generate the focus and have it traverse the planned trajectory. Because no plan is perfect, real-time data (e.g., imaging data) obtained during treatment may enable the controller 210 to modify the planned trajectory in order to accommodate actual conditions encountered as treatment is applied.

Figure 2B:
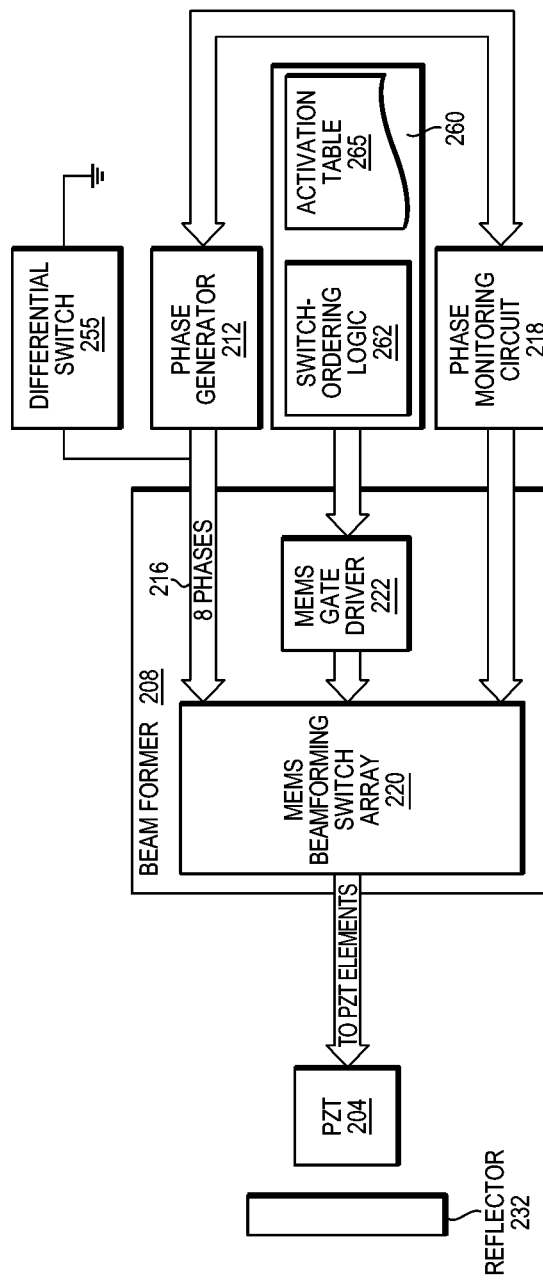

In various embodiments, each beamforming switch, upon activation (i.e., when "closed"), electrically couples a phase transmission line 216 to a transducer element 206. The MEMS gate drivers 222 set the relative phases of the signals driving the transducer elements 206 such that when individual transducer elements 206 are driven with corresponding settings, a focused ultrasonic beam is collectively produced at a desired location (e.g., the target location 102). With reference to FIG. 2B, in one embodiment, the phase transmission lines 216 are simplified by limiting the phase values available to the elements 206 to a number of discrete values. For example, there may be eight phase transmission lines 216 having eight "basis" signals corresponding to phase values of $\varphi_1, \varphi_2, \varphi_3, \ldots \varphi_8$, respectively; the eight phase values collectively cover the range 0 to $2\pi$. Each transducer element 206 may thus be driven by one of the eight phase values. This approach may advantageously reduce circuit complexity and expense. In addition, the beamformer 208 and/or the controller 210 may cause the phase generator 212 to change the phase value in each transmission line 216. For example, the eight phase transmission lines 216 may have phase values of $\varphi_1+\Delta\varphi, \varphi_2+\Delta\varphi, \varphi_3+\Delta\varphi, \ldots \varphi_8+\Delta\varphi$, respectively.

Various approaches may be employed to drive the transducer elements 206 with the desired phase values. For example, each transducer element 206 may be coupled, via the beamforming switch 220, to only one of the phase transmission lines 216, i.e., the one that has the desired phase value. By selectively coupling, via the beamforming switches, selected ones of the phase transmission lines to the transducer elements, the focused beam can be steered along various paths and/or at various target locations.

Figure 2C:
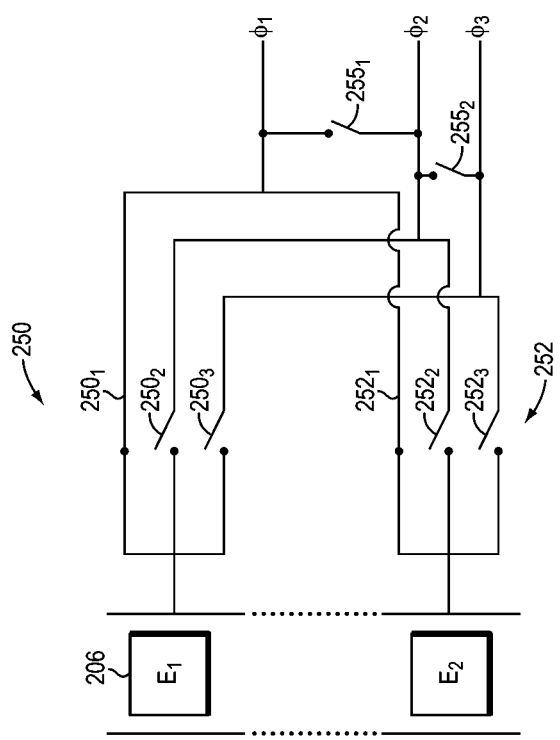
FIGS. 2C and 2D illustrates representative sets of beamforming switches and differential switches for driving transducer elements with various phase values in accordance with various embodiments.

FIG. 2C illustrates a representative organization and operation of the beamforming switches 220. For simplicity, two transducer elements 206 are labeled $E_1$ and $E_2$, and are shown as driven by three (rather than eight) phase-separated basis signals $\varphi_1, \varphi_2, \varphi_3$. The transducer elements $E_1$ and $E_2$ are selectively coupled to the signals by dedicated sets of beamforming switches 250, 252, respectively—that is, each set of switches 250, 252, although located within the switch matrix 220, is dedicated to a particular transducer element. In FIG. 2C, switches 250₁ and 252₁ are closed and the other switches are open, so $E_1$ and $E_2$ receive only the signal $\varphi_1$. Other transducer elements may receive different signals or combinations thereof, or no signal at all, depending on the state of the switch sets associated therewith. The switches 250, 252 may be electrical switches (e.g., transistors) and/or mechanical switches. In one implementation, the switches 250, 252 are MEMS switches. In another implementation, the switches 250, 252 are CMOS switches. Alternatively, the switches 250, 252 may include a combination of MEMS switches and CMOS switches.

The transducer elements (including elements $E_1$, $E_2$) may form a single contiguous area of the transducer surface, or include multiple non-contiguous surface portions. The switch sets dedicated to the various transducer elements are separately controllable, i.e., each transducer element is independently capable of emitting ultrasound pulses with frequencies and/or phases that are independent of the frequencies and/or phases of the other elements so as to achieve a treatment goal at the target region 102.

Acoustic pulses transmitted from the transducer elements 206 (or groups of the transducer elements) may traverse an ultrasound medium and/or intervening tissue located between the transducer array 204 and target region 102 prior to generating a focal zone at the target region 102. The inhomogeneity of the ultrasound medium and/or intervening tissue may, however, cause acoustic aberrations in the pulses, decrease the intensity of the acoustic energy at the focal zone, distort the focal profile, and may even move the location of the focal zone. Accordingly, in various embodiments, the phase shifts of the transducer elements (or groups of transducer elements) are adjusted in order to account for the acoustic aberrations. In addition, the phase shifts of the transducer elements are adjusted in order to steer the focal zone to different locations. This approach may be necessary when the target region spans a large volume such that disruption of multiple sub-regions, each corresponding to a focal zone, is necessary and/or when multiple target regions are identified for treatment.

To adjust the phase shifts of the transducer elements, the beamforming switches associated with the transducer elements may be deactivated (or "opened") to disconnect the transducer elements 206 from currently coupled phase transmission lines 216 and subsequently activated (or "closed") to connect the transducer elements 206 to the phase transmission lines 216 that have phase shifts corresponding to the desired new values determined by the controller 210. In this situation, a voltage may be present on the switches and render them vulnerable to premature failure. With reference to FIG. 2C, suppose that the switch pattern is to be reversed, i.e., presently closed switches $250_1$, $252_1$ are to be opened and the other switches $250_2$, $252_2$, which are both open, are to be closed. In one approach, the output voltage level of the AC signal source 214 (see FIG. 2A) is brought closer to zero than, for example, ±0.5V RMS. Additionally, to mitigate voltage-induced harm to beamforming switches, an approach termed "make before break" may be applied. In this approach, currently open beamforming switches (e.g., switches $250_2$, $252_2$) that will later be closed in accordance with a new switch pattern are closed before the currently closed beamforming switches (e.g., switches $250_1$, $252_1$) that will later be opened change state. In this way, the beamforming switches associated with each transducer element will be at substantially the same voltage (even if this voltage is not zero volts) before any switches are opened. This advantageously avoids sharp peak voltage differences among the beamforming switches that could occur as a result of phase differences. In some embodiments, closing of the beamforming switches occurs sequentially on an element-by-element basis. For example, the switch $252_2$ associated with the transducer element $E_2$ may be closed only after the switch $250_2$ associated with the transducer element $E_1$ is closed; and the beamforming switch associated with a transducer element $E_3$ (not shown) may be closed only after the switch $252_2$ associated with the transducer element $E_2$ is closed, and so on. The closing pattern of the beamforming switches may be determined by a switch-ordering logic in accordance with the switch-coupling strategies as further described below so as to avoid (or at least reduce) damage to the earlier-closed switches.

Figure 2D:
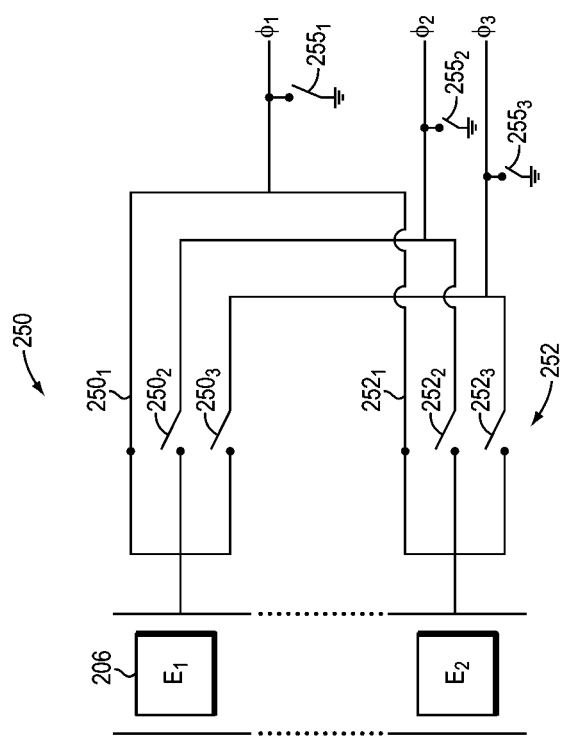

Additionally or alternatively, the outputs of the different phase transmission lines 216 may be progressively coupled, one to the next, so that the potential between switches will not be affected by phase differences. This sequential coupling may occur prior to the make-before-break process described above and may take place at the phase generator 212 or by the (optional) differential switches 255 implemented within, or in some embodiments separate from, the switch matrix 220 and associated with the different switch sets of the beamforming switches; each differential switch 255 is associated with a phase transmission line 216 and may couple the phase transmission line to ground, a common voltage, or another transmission line. Accordingly, implementation of the differential switches 255 provides at least two approaches for minimizing the voltage difference between the phase transmission lines—i.e., by coupling the phase transmission lines to one another or by coupling the phase transmission lines to a common voltage or ground (as shown in FIG. 2D). Each approach alone may be sufficient to minimize the voltage difference, but the two approaches can be combined as well. If the voltage level of the AC source 214 is driven low enough, however—for example, by grounding all signal lines 216 with one or more differential switches 255—and the maximum peak-to-peak potential between beamforming switches does not exceed, for example, ±0.5V, it may not be necessary to connect the phase transmission lines together.

With the voltage at all beamforming switches sufficiently low that a change in the open/closed switch pattern will not subject any switch to a voltage greater in magnitude than ±0.5V, the switch pattern may be changed (e.g., with reference to the above example, switches $250_1$, $252_1$ are opened and switches $250_2$, $252_2$ are closed). Still, the controller 210 may delay changing the beamforming switch states for a short interval to ensure settling and safe operation. The necessity for and duration of the interval may be determined by sonication parameters (such as amplitudes of the applied ultrasound pulses) and/or environmental conditions (such as RF signals, reflections from the transducer elements, and/or thermal or mechanical stress). In general, the duration will range from 1 microsecond to 1 millisecond. In one implementation, the delay continues until a substantial portion (e.g., 90%, 80% or 70%) of the reflection energy has dissipated.

The order of closing the beamforming switches described above can be important, because the first beamforming switch that is closed will experience a higher peak-to-peak voltage than succeeding beamforming switches. Accordingly, if any particular beamforming switch 250/252 in the switch matrix 220 is closed first too frequently relative to the other beamforming switches, it will wear out faster. In addition, the closing pattern of the differential switches 255 may be important, because the first differential switch 255 connecting different phase transmission lines that are coupled may also experience a higher peak-to-peak voltage than succeeding switches, since with each new switch coupling, more phases are added, leading to more amplitude cancellation.

Accordingly, referring again to FIG. 2B, in one embodiment, the controller 210 includes or communicates with a beamforming module 260, which includes circuitry or executable program code implementing switch-ordering logic 262 and an activation table or database 265 in computer memory or a mass-storage device. The activation table 265 keeps a running log of switch activation patterns associated with the differential switches 255 and/or the beamforming switches that are closed during the make-before-break process. In one implementation, for example, the activation table 265 stores, for each differential switch 255 and/or each beamforming switch of the switch matrix 220, its ordinal place in each switch-coupling sequence. In another implementation, the activation table 265 only stores an updated value corresponding to the number of times each differential switch 255 has been the first switch connecting two phase transmission lines 216 together and/or an updated value corresponding to the number of times each beamforming switch has been the first one that is closed during the make-before-break process. Based on the records stored in the activation table 265, the switch-ordering logic 262 determines, for each switch set, the order of coupling or, in simpler implementations, which beamforming switch should be closed first and/or which pair of the phase transmission lines 216 should be coupled first—i.e., which differential switch 255 in each set should be closed first (on the assumption that the first switch coupling is more harmful to the switches than subsequent couplings). That is, the switch-ordering logic 262 may arrange the closing order for each switch pattern transition so that, cumulatively, none of the beamforming switches and/or differential beamforming sustains an excessive voltage burden; for example, the ordinal place of each beamforming switch 250/252 in the switch-closing sequences may be averaged or balanced among the switches. Alternatively, instead of balancing the voltage burden among the beamforming switches 250/252 as described previously, the switch-ordering logic 262 may deliberately overburden certain differential switches 255 designated as sacrificial. This is particularly suitable when coupling of the phase transmission lines occurs prior to closing of the beamforming switches that are to be closed in the new switch pattern. These sacrificial switches may reside on a separate board or chip that is easily replaced, and may in fact be scheduled for periodic, prophylactic replacement.

In some embodiments, the phase shifts associated with the transducer elements (or groups of transducer elements) are adjusted substantially simultaneously—i.e., the output voltage of the signal generator 212 may be first decreased so as to reduce the differential voltages between the phase transmission lines connected to the currently activated transducer elements 206. The differential switches 225 associated with the currently activated transducer elements and designated to be closed first are then substantially simultaneously activated to connect two phase transmission lines together for all activated transducer elements. The differential-switch activation process is progressively performed until all transmission lines (or at least the ones that are connected to the activated transducer elements) are connected together. Using this approach, the first-closed differential switches corresponding to the currently activated transducer elements may experience the same amount of voltage burden.

Figure 2E:
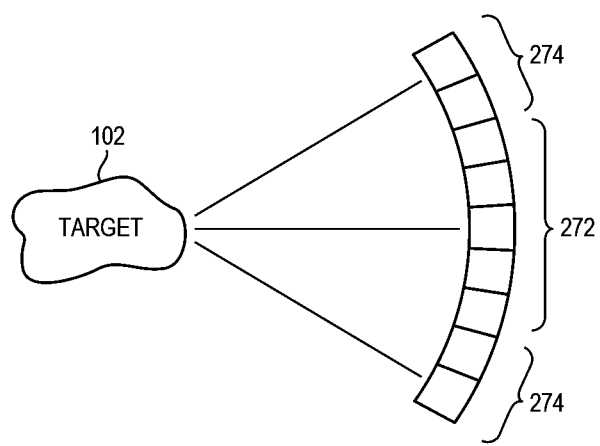
FIG. 2E depicts a focused ultrasound system including transducer elements making different contributions to an acoustic energy at a target region in accordance with various embodiments.

It may, however, be desirable to reduce the voltage burden on the switches associated with transducer elements that contribute significantly to the acoustic energy at the target region 102. In various embodiments, the closing order of the beamforming switches is determined based in whole or in part on the geometry (e.g., locations) of the transducer elements. For example, referring to FIG. 2E, transducer elements 272 located at the center region (as defined below) of the transducer may contribute more acoustic energy at the target region 102, while transducer elements 274 located at the outer region of the transducer may contribute less, as the acoustic energy emitted therefrom is largely reflected or absorbed by the ultrasound medium located between the transducer elements 274 and the target region 102. Accordingly, the switch-ordering logic 262 may arrange the beamforming switches 250, 252 associated with the transducer elements 274 to be closed prior to the beamforming switches associated with the transducer elements 272. Again, such a switch pattern may be stored in the activation table 265 and be retrieved therefrom at a later time. As used herein, the "center region" may include all transducer elements 206 except the elements forming the periphery of the transducer array 204. Alternatively, the "center region" may include elements located within an area that is only a fraction of the radial extent—e.g., 10%, 20%, 50%, etc. The "outer region" typically includes all elements 206 outside the center region.

Figure 3A:
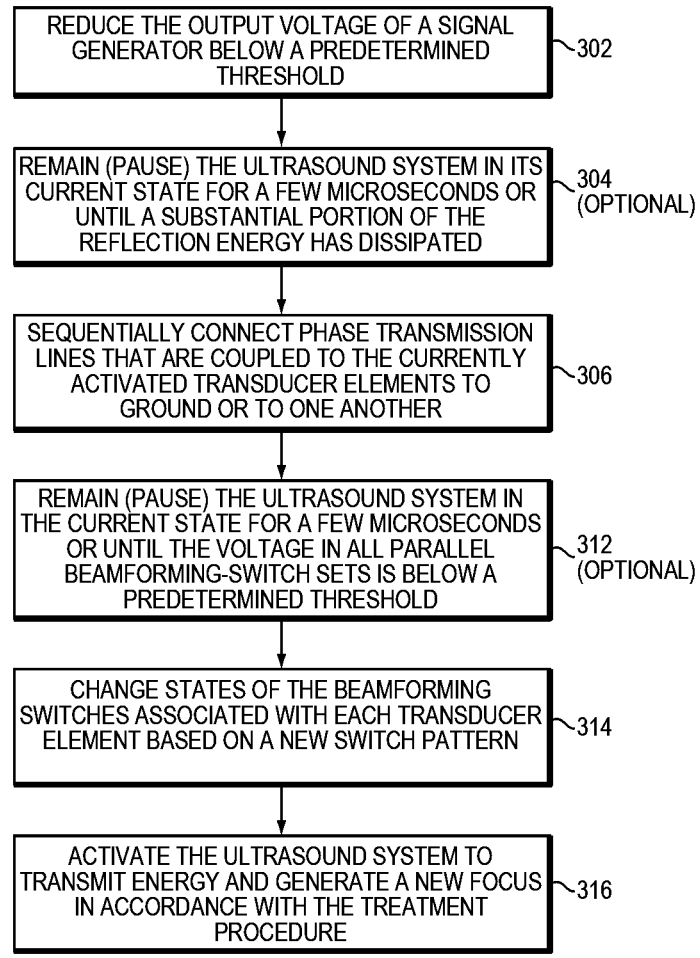
FIGS. 3A and 3B are flow charts illustrating various approaches for improving reliability in an ultrasound system having a switch matrix in accordance with various embodiments.
Figure 3B:
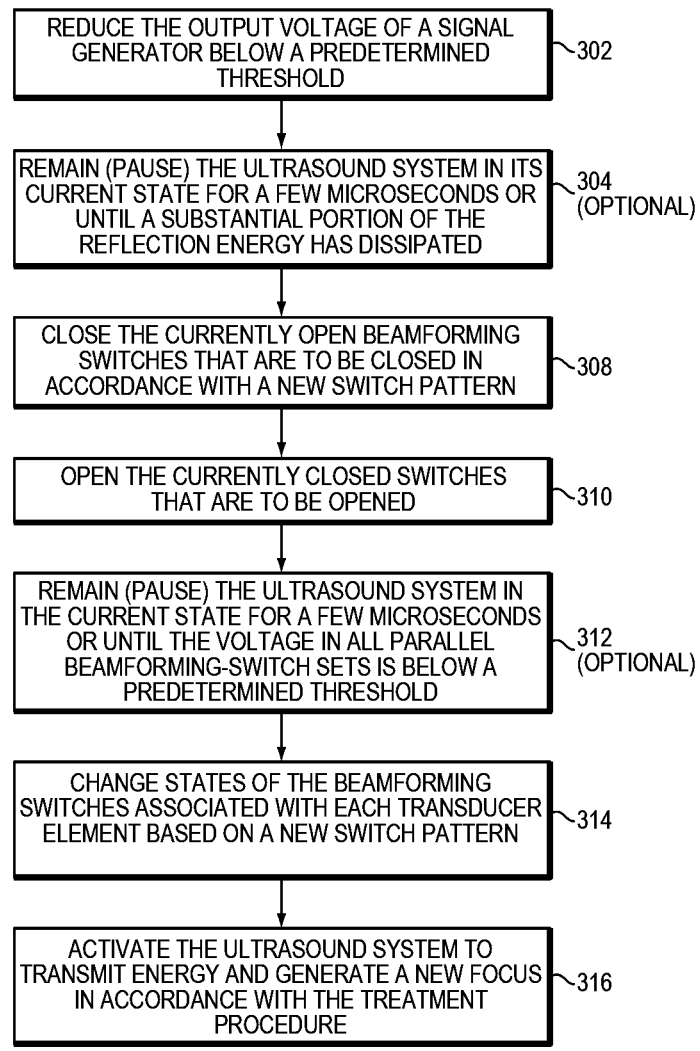

FIGS. 3A and 3B are flow charts illustrating two exemplary approaches for improving reliability in an ultrasound system having a switch matrix in accordance with various embodiments. In a first step 302, the output voltage of the signal generator 212 is reduced below a predetermined threshold (e.g., ±0.5V). In a second step 304, the ultrasound system may optionally remain in its current state for a few microseconds until a substantial portion (e.g., 90%, 80% or 70%) of the reflection energy has dissipated. In a third step 306, the phase transmission lines (each associated with a beamforming switch) connected to currently activated transducer elements may be sequentially grounded or coupled to one another using, for example, differential switch sets. Alternatively or additionally, the currently open beamforming switches that are to be closed in accordance with a new switch pattern are closed (in a step 308); and subsequently, the currently closed switches that are to be opened are opened (in a step 310). (In embodiments where steps 306, 308, 310 are performed, step 306 may be performed before or after steps 308, 310.) Again, the ultrasound system may then optionally remain in such a state for a few microseconds until the voltage in all parallel beamforming-switch sets is below a predetermined threshold (e.g., closer to zero than, for example, ±0.5V (or less)) or the switches can be assumed to have settled (in a step 312) after a fixed interval. The beamforming switches associated with each transducer element then change their states in accordance with the changed switch pattern such that different combinations of basis signals are now connected to the transducers to produce a focus at a new target location (in a step 314). The ultrasound system is then ready to transmit energy to the new focus in accordance with the treatment procedure (in a step 316).

In general, functionality for performing switch-coupling or -closing strategies, whether integrated within the controller 210 of the ultrasound system 200, or provided by a separate external controller, may be structured in one or more modules implemented in hardware, software, or a combination of both. For embodiments in which the functions are provided as one or more software programs, the programs may be written in any of a number of high level languages such as FORTRAN, PASCAL, JAVA, C, C++, C#, PYTHON, BASIC, various scripting languages, and/or HTML. Additionally, the software can be implemented in an assembly language directed to the microprocessor resident on a target computer (e.g., the controller); for example, the software may be implemented in Intel 80×86 assembly language if it is configured to run on an IBM PC or PC clone. The software may be embodied on an article of manufacture including, but not limited to, a floppy disk, a jump drive, a hard disk, an optical disk, a magnetic tape, a PROM, an EPROM, EEPROM, field-programmable gate array, or CD-ROM. The beamforming modules 260 may also be programmed in any suitable programming language, including, without limitation, high-level languages such as C, C++, C#, Ada, Basic, Cobra, Fortran, Java, Lisp, Perl, Python, Ruby, or Object Pascal, or low-level assembly languages. Embodiments using hardware circuitry may be implemented using, for example, one or more FPGA, CPLD or ASIC processors. The system components or parts thereof described herein may be constructed in one location and directly coupled to each other or, alternatively, distributed and connected to each other by means of PWB, connectors and/or cables.

In addition, the term "controller" used herein broadly includes all necessary hardware components and/or software modules utilized to perform any functionality as described above; the controller may include multiple hardware components and/or software modules and the functionality can be spread among different components and/or modules.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A method of improving reliability in an ultrasound system comprising (i) a plurality of transducer elements, (ii) a phase generator connected to a plurality of phase transmission lines, and (iii) a switch matrix comprising a plurality of beamforming switches for switchably connecting various ones of the phase transmission lines to the transducer elements, each of the transducer elements being associated with a set of beamforming switches each connected to a different phase transmission line, wherein some of the beamforming switches are open and some of the beamforming switches are closed in accordance with an initial switch activation pattern, the method comprising:
   (a) reducing the differential voltage between the phases at the phase generator;
   (b) reducing the differential voltage between the phases at near the beamforming switches; and
   (c) following steps (a) and (b), altering the initial switch activation pattern.

2. The method of claim 1, wherein the differential voltage in step (a) is reduced below a first predetermined threshold corresponding to a voltage closer to zero than ±0.5V.

3. The method of claim 1, wherein the differential voltage in step (b) is reduced below a second predetermined threshold corresponding to a voltage closer to zero than ±0.5V.

4. The method of claim 1, further comprising a step of pausing after performing steps (a) and (b) and before performing step (c).

5. The method of claim 4, wherein the pausing step has a duration determined by at least one of an environmental condition or a sonication parameter.

6. The method of claim 5, wherein the environmental condition is an ambient RF level.

7. The method of claim 5, wherein the environmental condition is reflection from the transducer elements.

8. The method of claim 5, further comprising the step of monitoring a voltage on a closed switch, wherein the environmental condition is a magnitude of the monitored voltage.

9. The method of claim 5, wherein the sonication parameter comprises an amplitude of a pulse transmitted from one of the transducer elements.

10. The method of claim 1, further comprising a step of pausing after performing step (a) and before performing step (b).

11. The method of claim 1, wherein step (b) is performed by progressively connecting the phase transmission lines together using a plurality of sets of differential switches, each differential switch being associated with at least one of the phase transmission lines.

12. The method of claim 11, wherein at least one of the beamforming switches or the differential switches is an MEMS switch.

13. The method of claim 11, wherein at least one of the beamforming switches or the differential switches is a CMOS switch.

14. The method of claim 11, wherein at least one of the differential switches or the beamforming switches in each set are sequentially activated in a predetermined order.

15. The method of claim 14, wherein the predetermined order is based on a previous switching order.

16. The method of claim 15, wherein the predetermined order is determined by a number of previous times each of the differential switches was the first differential switch coupling the associated phase transmission line to another phase transmission line when changing the initial switch activation pattern to a new switch activation pattern.

17. The method of claim 15, wherein the predetermined order is based on a number of previous times each of the differential switches in each switch set being a sacrificial switch.

18. The method of claim 15, wherein the predetermined order is determined by a number of previous times each of the beamforming switches was the first beamforming switch that was activated when changing the initial switch activation pattern to a new switch activation pattern.

19. The method of claim 1, wherein, in a set of the beamforming switches in which a first beamforming switch is closed and a second beamforming switch is open, step (c) comprises closing the second beamforming switch and, thereafter, opening the first switch.

20. The method of claim 1, wherein, in a set of the beamforming switches in which a first group of beamforming switches is closed and a second group of beamforming switches is open, step (c) comprises closing the second group of beamforming switches and, thereafter, opening the first group of beamforming switches, the beamforming switches in the second group being sequentially closed in a predetermined order.

21. The method of claim 20, wherein the predetermined order is based on a previous switching order.

22. The method of claim 21, wherein the predetermined order is determined by a number of previous times each of the beamforming switches in the second group was first to be closed.

23. The method of claim 20, wherein the predetermined order is based on a geometry of the transducer elements.

24. The method of claim 23, wherein the geometry comprises relative locations of the transducer elements in the ultrasound system.

\* \* \* \* \*